(12) United States Patent
Samarut et al.

(10) Patent No.: US 6,998,266 B2
(45) Date of Patent: *Feb. 14, 2006

(54) ACTIVE RETINOIC ACID-FREE CULTURE MEDIUM FOR AVIAN TOTIPOTENT EMBRYONIC STEM CELLS

(75) Inventors: Jacques Samarut, Lyons (FR); Bertrand Pain, Lyons (FR)

(73) Assignees: Institute National de la Recherche Agronomique, Paris (FR); Centre National de la Recherche Scientifique (CNRS), Paris (FR); Ecole Normale Superieur de Lyon, Lyons (FR)

(*) Notice: Subject to any disclaimer, the term of this patent is extended or adjusted under 35 U.S.C. 154(b) by 102 days.

This patent is subject to a terminal disclaimer.

(21) Appl. No.: 10/097,245

(22) Filed: Mar. 15, 2002

(65) Prior Publication Data

US 2002/0192815 A1 Dec. 19, 2002

Related U.S. Application Data (63) Continuation of application No. 09/392,506, filed on Sep. 1, 1999, now Pat. No. 6,500,668, which is a continuation of application No. 08/817,671, filed as application No. PCT/FR95/01389 on Oct. 20, 1995, now Pat. No. 6,114,168.

(30) Foreign Application Priority Data

Oct. 21, 1994 (FR) .......................... 94 12598

(51) Int. Cl.
C12N 5/02 (2006.01)

(52) U.S. Cl. ................. 435/406; 435/404; 435/405; 435/384

(58) Field of Classification Search ............. 435/384, 435/404–406, 325, 455
See application file for complete search history.

(56) References Cited

U.S. PATENT DOCUMENTS

| | | | | |
|---|---|---|---|---|
| 5,453,357 A | * | 9/1995 | Hogan | 435/7.21 |
| 5,589,458 A | | 12/1996 | Jameson et al. | |
| 6,114,168 A | * | 9/2000 | Samarut et al. | 435/405 |
| 6,500,668 B1 | * | 12/2002 | Samarut et al. | 435/383 |

FOREIGN PATENT DOCUMENTS

| | | |
|---|---|---|
| WO | 90/01541 | 2/1990 |
| WO | 93/15185 | 8/1993 |
| WO | WO 93/23528 | * 11/1993 |
| WO | WO 94/03585 | * 2/1994 |

OTHER PUBLICATIONS

Chang (Cell Bio. International, 1997, vol. 21, p. 495–499).*
Hayman (1993, Cell, vol. 74, p. 157–169).*
Bradley, 1992, Biotechnology, vol. 10, p. 534–539.*
Seamark, 1994, Reproductive Fertility and Devel., vol. 6, p. 653–657.*
Simkiss (1994, Maclean ed. Animals with novel genes, Cambridge Univ. Press, Cambridge, England; NY, NY, p. 106–137.*
Mullins (1996, J. Clin. Invest., vol. 98, p. S37–S40.*
Chang (Cell Biol. International, Jul. 1995, vol. 19, p. 569–576.*
Godin (Nature, 1991, vol. 352, p. 807–809.*
Definition of "murine".*
Terstappen, 1994, Blood cells, vol. 20, p. 45–64.*
Smith et al., "Buffalo Rat Liver Cells Produce a Diffusible Activity Which Inhibits the Differentiation of Murine Embryonal Carcinoma and Embryonic Stem Cells", Developmental Biology, May 1987, pp. 1–9, vol. 121, No. 1.
Slager et al., "Transforming Growth Factor–Beta in the Early Mouse Embryo: Implications for the Regulation of Muscle Formation and Implantation", Developmental Genetics, 1993, pp. 212–224, vol. 14, No. 3.
Freshney, Second Edition, "Culture of Animal Cells: A Manual of Basic Technique", pp. 187–196, Alan R. Liss, Inc., New York.
Smith, et al., Medline Abstract No. 87191399, "Buffalo Rat Liver Cells Produce a Diffusible Activity Which Inhibits the Differentiation of Murine Embryonal Carcinoma and Embryonic Stem Cells", Dev. Biol. 121:1–9 (May 1987).
Slager, et al., Medicine Abstract No. 93365092, "Transforming Growth Factor–Beta in the Early Mouse Embryo: Implications for the Regulation of Muscle Formation and Implantation", Dev. Genet. 14:212–24 (1993).
Terstappen et al., "Analysis of Bone Marrow Stem Cell", Blood Cells, 1994 (20): 45–64.
Seamark, R.F., "Progress and Emerging Problems in Livestock Transgenesis: a summary perspective", Reprod. Fertil. Dev., 1994, 6, 653–657.
Mullins, L.J. et al., "Perspectives Series: Molecular Medicine in Genetically Engineered Animals", J. Clin. Invest., 1996, (98): S37–S40.
Pain et al., Development, vol. 122, pp. 2339–2348.
Gibco Catalog, Gibco BRL, Gaithersburg, MD, pp. 139, 152, 166, 172, 180, 195 and 198.

* cited by examiner

*Primary Examiner*—Michael C. Wilson
(74) *Attorney, Agent, or Firm*—Heller Ehrman LLP

(57) ABSTRACT

A culture medium for avian embryonic cells and an avian cell culture medium is disclosed. The culture medium is characterized in that it has elements complementary to avian embryonic cells. The complementary elements include insulin-like growth factors and stem cell growth factors. The medium is substantially free of active retinoic acid. A method of culturing avian embryonic cells and the resulting products are disclosed.

11 Claims, 7 Drawing Sheets

(1 of 7 Drawing Sheet(s) Filed in Color)

ACTIVE RETINOIC ACID-FREE CULTURE MEDIUM FOR AVIAN TOTIPOTENT EMBRYONIC STEM CELLS

This application is a continuation of U.S. patent application Ser. No. 09/392,506, filed Sep. 1, 1999 now U.S. Pat. No. 6,500,668 which is a continuation of U.S. patent application Ser. No. 08/817,671 filed May 12, 1997 now U.S. Pat. No. 6,114,168, which is a 371 of PCT/FR95/01389 filed Oct. 20, 1995 (WO 96/12793).

The present invention relates to the obtaining of bird ES cells, especially to a method of culture and to a medium permitting the culture of these cells.

In effect, in the context of perfecting recombinant protein production technique, the development of a technique of transgenesis [sic] in domestic birds will have extremely important economic repercussions in two major applications:

1. the development of avian strains possessing particular genetic characters (resistance to certain diseases, growth performance features, and the like)
2. the development of recombinant protein production systems in egg albumin.

The biotechnology industry is showing increasing interest in the possibility of producing proteins of interest in biological fluids or organisms (blood, milk, plants, etc.). The production of such proteins in domestic birds' eggs will certainly constitute a major technological advance in this approach, for several reasons:

numerous mammalian proteins cannot be produced in a mammalian system because their overabundance in these organisms has deleterious effects (for example erythropoietin, which induces pathological hyperglobulinemia in rabbits). Many of these proteins of interest do not display cross-activity with those of birds, thus permitting their overproduction in an avian organism without major pathological effect;

it is very probable that the marketing of recombinant proteins produced in mammals will come up against health problems associated with the presence in this [sic] species of latent organisms which are potentially pathogenic for man (lentiviruses, prions, etc.). This risk is very minimal, not to say almost nonexistent, in relation to pathogenic agents of domestic birds;

the egg constitutes a "tissue" which is very dense with respect to a small number of proteins. For example, the major protein of birds' eggs, ovalbumin, represents 54% of the egg white proteins, equivalent to an average dry weight per egg of 2 grams of dry matter approximately. It is possible reasonably to conceive of producing per egg at least 10% of this mass as recombinant protein. The economic viability is seen to be very great if it is considered that a hen lays on average 2 eggs every three days, and this viability is seen to be much greater than that of large mammals if the much lower breeding costs of domestic birds are considered.

The production of transgenic birds is currently possible at an extremely high cost on account of its very low efficiency. In effect, in birds, the technique of microinjection of DNA into the egg is almost impossible. On the other hand, the use of the vector retrovirus system, the only efficient system to date, remains complex and will certainly come up against a reticence on the part of industrialists on health grounds.

A very great advance in the production of transgenic animals has been brought about in mice by the development of ES cell technology.

ES cells (embryonic stem cells) are totipotent embryonic cells capable of regenerating all the tissues of the embryo, including the germ tissue, after their injection into very early embryos. These cells may hence be considered to be Trojan horses for introducing new genetic information into an animal's genetic constitution. The possibility of culturing these cells in the long term in vitro affords the possibility of exercising numerous controls before their implantation in vivo. Moreover, these cells may be stored without limit in liquid nitrogen, which constitutes a potential for storage of a genetic constitution.

The use of ES cells nowadays constitutes the most promising approach in domestic birds for the efficient production of transgenic animals.

Recent work from a Canadian group (R. Etches at the Guelph station) has suggested that ES cells must exist in the bird embryo (Petitte et al., 1990). This group at [sic] succeeded in transplanting such cells into embryos and consequently producing animals whose genetic constitution is derived from that of the grafted cells. However, to date, it has not been possible for success to be achieved in culturing these cells in vitro; as a result, it has not been possible to use these cells to transfer a transgene in a stable manner. This is a major impediment to the exploitation of ES cell technology in birds. ES cells may be characterized by three essential types of criteria:

morphology endogenous alkaline phosphatase activity reaction with antibodies which are specific for a state of totipotency (ECMA-7, SSEA-1 and SSEA-3, in particular).

To date, it has not been possible to obtain any culture of ES cells which are identified by these collective characteristics.

Accordingly, the subject of the present invention is a culture medium for avian totipotent embryonic cells, of the type containing an avian cell culture medium, characterized in that it contains components supplementary to said avian cell culture medium, said supplementary components being chosen from the group comprising: cytokines, fibroblast growth factors, insulin-like growth factors and stem cell growth factors, and in that it is substantially free from active retinoic acid.

Advantageously, the retinoic acid is substantially inactivated by anti-retinoic acid antibodies (ARMA) present in the medium.

In effect, the media employed often contain serum, in which the amount of endogenous retinoic acid cannot be controlled. On testing the effect on cell differentiation of incorporating in the culture medium an anti-retinoic acid monoclonal antibody which would neutralize the action of retinoic acid, the Applicant found that the presence of this antibody increases the presence in the cultures of cells and colonies having alkaline phosphatase activity.

The cytokine may be chosen, in particular, from LIF, IL-11, IL-6, CNTF and oncostatin M (OSM); advantageously, the cytokines present in the culture medium described above comprise at least one cytokine chosen from the group consisting of LIF, IL-11, IL-6 and the various mixtures thereof, which give the best results for growth stimulation.

Preferably, the fibroblast growth factor is b-FGF (or basic fibroblast growth factor) and the insulin-like growth factor is IFG-1.

The stem cell growth factor (or SCF) is preferably a-SCF (or avian stem cell factor) and m-SCF (or murine stem cell factor).

One of the preferred aspects of the invention relates to a culture medium which contains, besides the basic nutrient components necessary for cell growth, a combination of b-FGF, SCF and LIF. In addition, the presence in the medium of a monoclonal antibody which neutralizes the differentiation activity exerted by retinoic acid increases the number of totipotent embryogenic stem cells.

The presence of a lawn of feeder cells promotes the growth of avian ES cells. Various cell types known to a person skilled in the art may be used; there may be mentioned especially cells such as STO cells, treated with mitomycin or irradiated, BRL-3A cells, LMH cells, QT6 cells and modified QT6 cells such as QT6 Isolde cells, differentiated cells established as a line from cultures of embryonic stem cells induced to differentiate.

STO cells are mouse embryo fibroblasts (ATCC catalogue); BRL-3A cells (ATCC catalogue) are liver cells from "Buffalo rat liver". QT6 cells (ATCC catalogue) and modified QT6 cells such as QT6 Isolde cells are quail fibroblasts (Cosset et al., 1990, J. Virol. 64, 10170-1078) and LMH cells originate from chicken liver carcinoma (Kawagucchi et al., 1987, Cancer Res., 47, 4460–4464).

The culture medium contains, in addition, various essential nutrient components and antibiotics.

A culture medium which is especially suitable for the present invention possesses the following composition:

| BHK-21 | |
|---|---|
| Fetal bovine serum | 10% |
| Chicken serum | 2% |
| Conalbumin | 20 ng/ml |
| Nonessential amino acids | 1% |
| Sodium pyruvate | 1 mM |
| Nucleoside stock | 1% |
| Hepes (1 M) | 10 mM |
| β-Mercaptoethanol | 0.2 mM |
| Penicillin | 100 U/ml |
| Streptomycin | 100 µg/ml |
| Gentamicin | 10 ng/ml |

Additives

| | Final |
|---|---|
| bFGF | from 1 to 20 ng/ml |
| a-SCF | from 0.5% to 2% vol/vol |
| IGF-1 | from 5 to 50 ng/ml |
| LIF | from 1000 to 5000 U/ml of purified form, approximately equivalent to from 0.1% to 2% vol/vol of culture supernatant of transfected COS cells |
| IL-6 | from 5 to 50 ng/ml (approximately from 0.1% to 2% vol/vol of culture supernatant of transfected COS cells) |
| IL-11 | from 5 to 50 ng/ml (approximately from 0.1% to 2% vol/vol of culture supernatant of transfected COS cells) |

Advantageously, the bFGF concentration is greater than 5 mg/ml and the IGF-1 concentration is greater than 10 ng/ml. with the nucleoside stock consisting of the mixture:

| adenosine | 80 mg |
|---|---|
| guanosine | 85 mg |
| cytidine | 73 mg |
| uridine | 73 mg |

-continued

| thymidine | 24 mg |
|---|---|
| $H_2O$ | 100 ml | and Cos SN representing a culture supernatant of COS-7 cells transfected for transient expression with a vector for the expression of the cDNA of the factor in question, and is suitable for the culture of bird totipotent embryonic cells.

BHK21 medium (or MEM medium) is a culture medium which has been described, in particular, by McPherson, I., and Stoker (1962, Virology 16, 147).

Hepes is hydroxyethylpiperazineethanesulfonate.

According to another aspect, the subject of the invention is a method of culture of avian totipotent embryonic cells (or avian ES cells), characterized in that:
a) cells originating from blastoderm disks of fertilized eggs are suspended in an avian cell culture medium comprising, in addition, at least one compound chosen from cytokines, fibroblast growth factors, insulin-like growth factors and stem cell growth factors, and in which the retinoic acid is substantially inactivated,
b) a lawn of feeder cells or a gelatin-treated culture dish is inoculated with the suspension obtained after step a),
c) the cells are incubated for a specified period,
d) the cells in culture are removed and purified so as to recover bird ES cells.

Preferably, between steps c) and d), one or more additions of fresh medium identical to the one used in step a) are performed at intervals of time.

In one of its embodiments, during step c), a reinoculation of the medium with a cell suspension identical to the suspension prepared in step a) is performed.

The medium of step a) preferably contains the following components: b-FGF, a-SCF, IGF-1, LIF, IL-11, IL-6 and anti-retinoic acid antibodies. According to one of the aspects of the invention, it contains, in addition, the following compounds:
Fetal bovine serum
Chicken serum
Conalbumin
Nonessential amino acids
Sodium pyruvate
Nucleoside stock
Hepes (1 M)
β-Mercaptoethanol
Penicillin
Streptomycin
Gentamicin
with the nucleoside stock consisting of the mixture: adenosine, guanosine, cytidine, uridine and thymidine in aqueous solution.

Optionally, during the method of the invention, between steps c) and d), the addition of fresh medium is performed on day 3 and the medium is then changed every day until the next subculturing.

Step d) may be performed, in particular, by enzymatic treatment, washing in a medium not containing any growth factor and centrifugation.

It is possible to collect directly the primary cell cultures, which will then be frozen, or alternatively to produce successive secondary cultures from the cells of the primary culture. In this case, after step d), a step e) is performed in which the ES cells are reinoculated onto a lawn of feeder cells, or onto gelatin-treated dishes, so as to obtain a secondary culture.

Steps d) and e) may be repeated several times in order to have tertiary and successive cultures.

The lawn of feeder cells can consist of various cell types described above, and in particular of mitomycin-treated or irradiated STO cells.

Another of the subjects of the invention is a culture of bird ES cells, or avian ES cells, which are capable of being obtained by the method defined above. A modified avian totipotent embryonic cell can be obtained by integration of the gene coding for a heterologous protein in the genome of an avian ES cell in culture.

Lastly, a method of production of a recombinant protein, characterized in that the gene coding for said protein is integrated in the genome of an avian totipotent embryonic cell in culture, is also included in the invention.

The Applicant has perfected a culture medium and in vitro culture conditions which make it possible to maintain in culture bird cells which possess morphological, kinetic and histochemical properties recalling those of totipotent embryonic cells. These observations have been made with cells derived from both quail and chicken blastoderm disks. The growth of these cells in culture in vitro is made possible by the perfecting of a novel medium especially adapted to the culture of bird embryonic cells. The presence, maintenance and propagation of totipotent cells in culture are known to permit their injection into recipient embryos. The contribution to the morphogenesis of the somatic and germ tissues in the recipient animals as a result of a totipotent character may lead to the obtaining of transgenic animals.

The patent or application file contains at least one drawing executed in color. Copies of this patent or patent application publication with color drawing(s) will be provided by the U.S. Patent and Trademark Office upon request and payment of the necessary fee.

The examples which follow are intended to illustrate the invention without in any way limiting its scope. In these examples, reference will be made to the following figures:

FIG. 2: Effect of anti-retinoic acid antibody (ARMA)

quail blastoderms, 0.75 bl/ml base with or without gelatin 4-d culture

FIG. 4: Comparison of an inoculation onto gelatin and onto a lawn of mitomycin C-treated cells in the presence of various cytokines all belonging to the same family.

4A: quail blastoderms, 1+1.5 bl/ml base with gelatin

3–+4-d culture

4B: quail blastoderms, 1+1.5 bl/ml base with STO cells

3–+4-d culture

2–+3-d culture

2–+3-d culture

Materials and Methods

Preparation of Cells

Freshly laid, unincubated hens' eggs correspond to stage X of development (Eyal Giladi and Kovak, 1976); "C. coturnix japonica" quails' eggs are also used from the time of laying and unincubated.

The blastoderm disk (3–4 mm in diameter for the hen, 2–2.5 mm for the quail) is removed using a Pasteur pipette in complete medium without factors. The cells are centrifuged at 200 g, washed twice in medium in order to remove as much contaminating vitellus as possible, resuspended on the basis of 2 disks per ml of medium and dissociated mechanically by passage through a 23 G needle. The factors are then added.

The cell suspension is applied:

either to dishes or wells (Costar) pretreated with gelatin (0.2% gelatin, 1 h at room t), or to a lawn of STO cells pretreated with mitomycin C (90 min, 37° C., 5 µg/ml) and reinoculated on the basis of $10^5$ cells/cm$^2$, or to a lawn of Isolde cells pretreated with mitomycin C (90 min, 37° C., 5 µg/ml) and reinoculated on the basis of $10^5$ cells/cm$^2$.

STO Culture Medium

| DMEM | final |
| --- | --- |
| Fetal bovine serum | 10% |
| Penicillin | 100 U/ml |
| Streptomycin | 100 µg/ml |
| L-Glutamine | 2 mM |

Isolde Culture Medium

| DMEM | final |
| --- | --- |
| Fetal bovine serum | 8% |
| Chicken serum | 2% |
| Penicillin | 100 U/ml |
| Streptomycin | 100 µg/ml |
| G418 | 100 µg/ml |
| Hygromycin | 50 µg/ml |
| Phleomycin | 50 µg/ml |
| TBP (tryptose phosphate broth) | 10% |

The selection drugs are added for maintenance but removed two days before treatment with mitomycin C.

In all cases, a second inoculation is carried out under the same conditions after two days of culture.

Cultures

The cultures are incubated at 37° C. or at 41° C. in a controlled $Co_2$ (7.5%) atmosphere, and their progress is monitored with a phase contrast microscope. A partial addition (50%) of fresh medium with the factors is carried out on day 3 of culture, and the medium is then changed every day. At each timepoint, the growing cells may be either fixed for study, or removed and reinoculated for secondary or higher culture onto a lawn of irradiated mitomycin-treated STO cells or onto gelatin-treated dishes.

In the case of fixation, the cells are washed twice in Tris-glucose and then fixed in situ for 15 min in 4% paraformaldehyde solution in the cold state (0–4° C.). After several washes with PBS, various stains may be applied according to one of the following protocols:

detection of endogenous alkaline phosphatase activity

| reaction buffer: | NaCl | 100 mM |
|---|---|---|
| | Tris-HCl pH 9.5 | 100 mM |
| | $MgCl_2$ | 5 mM |
| | NBT | 1 mg/ml |
| | BCIP | 0.1 m/ml [sic] |
| | $H_2O$ | |

(reading time from 5 to 30 min, 37 °C.)
detection of exogenous β-galactosidase activity

| reaction buffer: | K ferricyanide | 5 mM |
|---|---|---|
| | K ferrocyanide | 5 mM |
| | $MgCl_2$ | 5 mM |
| | X-gal | 1 mg/ml |
| | PBS | |

(reading time from 1 to 2 hours, 37°C.)
immunocytochemical detection of the presence of specific epitopes (reaction at 4° C.)

| blocking in PBS buffer-BSA | (1 mg/ml) |
|---|---|
| washing in PBS-BSA | |
| primary antibody | 1/10 or 1/50 |
| fluorescent secondary antibody | 1/50 | detection is carried out under an inverted fluorescence microscope.

Subculturing

In the case of passage to secondary or successive culture, the cells are washed twice in Tris-glucose and then incubated for 10–30 min in an enzyme solution. It is possible to use a solution of collagenase-dispase (1 mg/ml, equivalent to 1 U/ml final) to which a solution of hyaluronidase (1 mg/ml final, equivalent to 1 U/ml) may be added; it is also possible to use a solution of pronase at a final concentration of 0.25 mg/ml. The cells or small clumps of cells thus isolated enzymatically are washed in ESA medium, resuspended, placed on a cushion of lymphocyte separation medium of density (d=1.077–1.080) and centrifuged for 20 min at room t at 800 g in order to rid the undifferentiated blatoderm [sic] cells of the cells of the lawn, miscellaneous debris and contaminating residues of vitellus. The interface is then withdrawn and washed twice in ESA medium. The cell pellet obtained is resuspended and gently dissociated mechanically before being inoculated onto a fresh lawn of feeder cells, as described above. The equivalent of 6 initial blastoderm disks is reinoculated in 2 ml. Sometimes this gradient step is not necessary during successive passages, in accordance with the very great homogeneity of the cultures obtained.

The dissociated cells may be applied to a multilayer Percoll gradient and centrifuged under the same conditions. The interfaces are then withdrawn and washed in ESA medium, and the most immature cells of the upper interfaces reinoculated or injected into recipient embryos.

Freezing

After primary or successive culture, the cells recovered from the gradient may be frozen in a mixture consisting of 40% FBS, 50% ESA medium and 10% DMSO. Cells equivalent to 24 initial blastodisks are taken up in 0.5 ml of ESA medium and resuspended, and 0.4 ml of serum is added. 0.1 ml of DMSO is then added very slowly. The suspension for freezing is distributed in freezing tubes (0.5 ml/tube) and frozen slowly at −80° C. before being transferred to liquid nitrogen.

Results

A basal medium referred to as "ESA", for "embryonic stem cells avian", medium, derived from a medium used for murine ES cells, was prepared. It possesses the following composition:

"ESA" Medium

| BHK-21 | final |
|---|---|
| Fetal bovine serum | 10% |
| Chicken serum | 2% |
| Conalbumin | 20 ng/ml |
| Nonessential amino acid [sic] | 1% |
| Sodium pyruvate | 1 mM |
| Nucleoside stock | 1% |
| Hepes (1 M) | 10 mM |
| β-Mercaptoethanol | 0.2 mM |
| Penicillin | 100 U/ml |
| Streptomycin | 100 µg/ml |
| Gentamicin | 10 ng/ml |

To this "ESA" basal medium, growth factors were added in order to compare their respective contribution to the formation of colonies displaying a morphological and biochemical character of interest. Their concentrations are shown below:

Additives

| | stock | final |
|---|---|---|
| bFGF | 10 µg/ml | 10 ng/ml |
| a-SCF | trans Cos SN* | 1% vol/vol |
| IGF-1 | 10 µg/ml | 20 ng/ml |
| LIF | trans Cos SN* | 1% vol/vol |
| IL-11 | 10 µg/ml | 10 ng/ml |
| IL-6 | 10 µg/ml | 10 ng/ml |
| ARMA | 10 mg/ml | 1 µg/ml |
| OSM | 20 µg/ml | 20 ng/ml |
| CNTF | 20 µg/ml | 20 ng/ml |
| nucleoside stock | | |
| | adenosine | 80 mg |
| | guanosane | 85 mg |
| | cytidine | 73 mg |
| | uridine | 73 mg |
| | thymidine | 24 mg |
| | $H_2O$ | 100 ml |

*culture supernatant of COS-7 cells transfected for transient expression with a vector for the expression of the cDNA of the factor in question.

The first criterion used to evaluate the effect of these factors and of the modifications made to the medium was the detection by biochemical staining of the endogenous alkaline phosphatase activity, which seems to be specific for a number of cells such as totipotent ES cells, precursor cells derived from the germ line and certain differentiated cells which can be readily identified with their epithelioid morphology.

Figure 1:
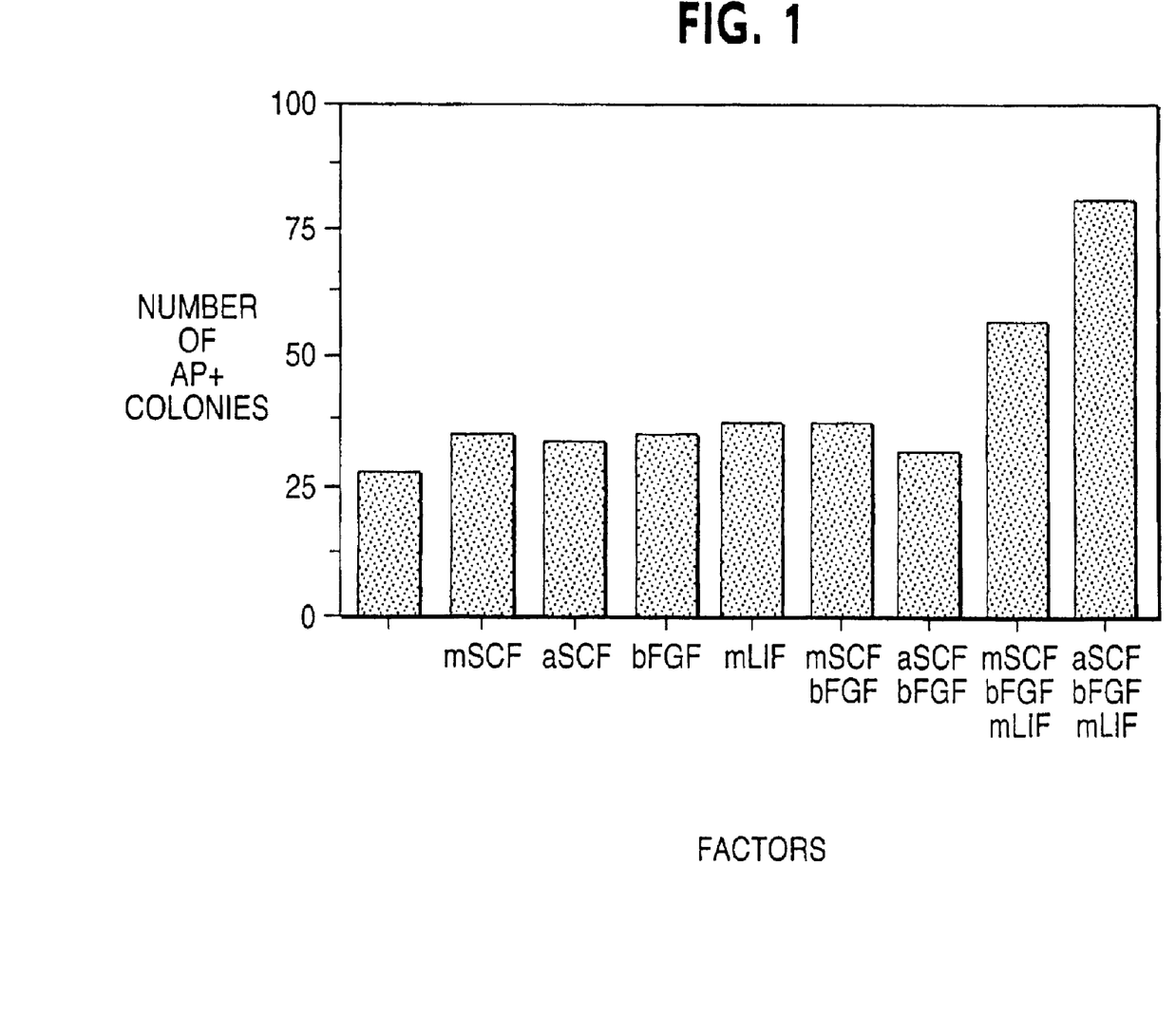
FIG. 1: Effect of the combinations of factors quail blastoderms, 0.75 bl/ml gelatin base 3-d culture

Blastoderm disk cells are inoculated in ESA medium in the presence of various combinations of factors. After 3 d of culture, the cells are fixed and stained and the colonies which are positive for alkaline phosphatase activity (AP+) are counted.

The effect of the various combinations of factors is depicted in FIG. 1.

Conclusion

Among the factors tested, the combination of SCF (stem cell factor of murine—mSCF—or avian—aSCF—origin), b-FGF (basic fibroblast growth factor) and LIF (leukemia inhibitory factor) gives the best number of colonies which are positive for alkaline phosphatase activity in the cultures, with a 2- to 3-fold increase relative to the presence of each factor added individually or in pairs and relative to the baseline level, consisting predominantly of weakly positive cells displaying a differentiated epithelioid morphology.

II) Effect of Anti-Retinoic Acid Antibody (ARMA)

Figure 2:
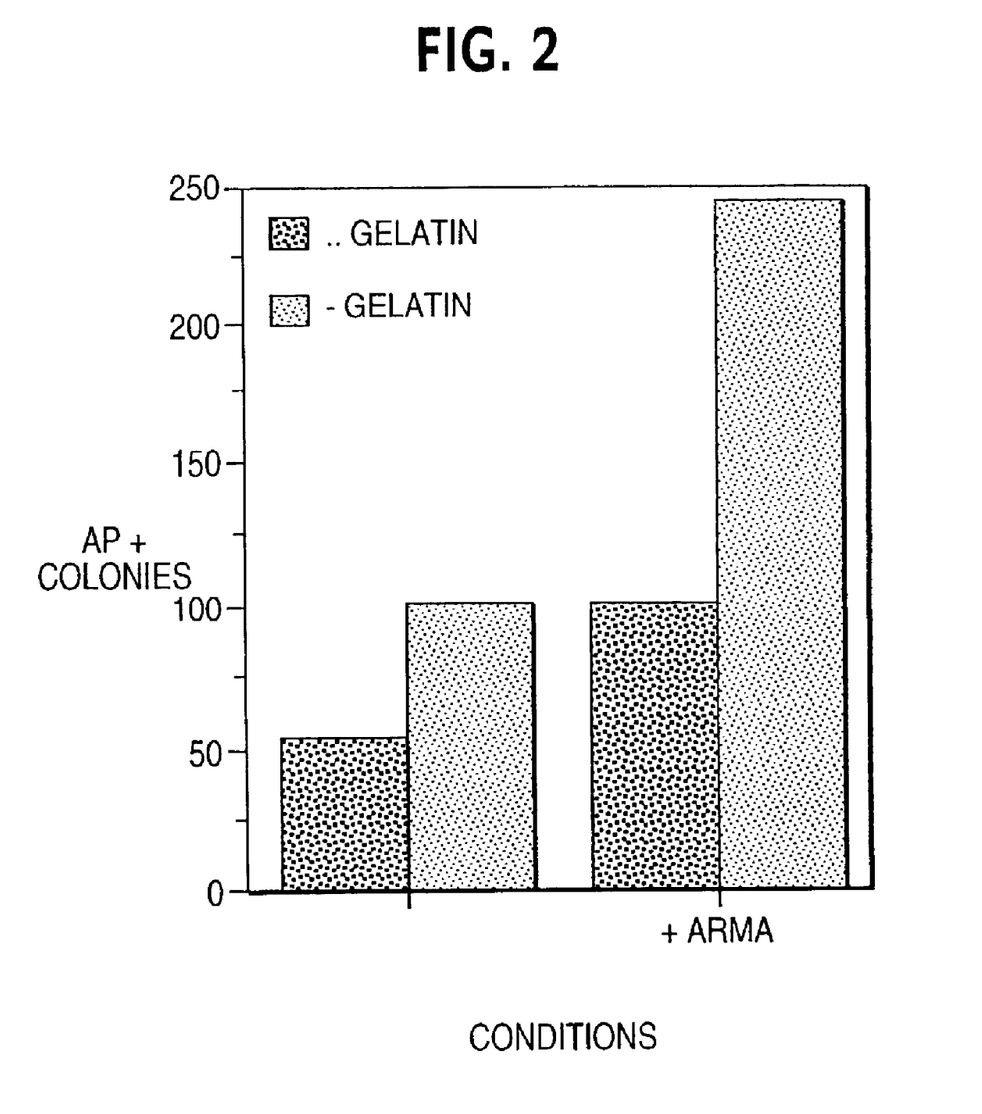

The cells are inoculated onto either untreated or gelatin-treated dishes in complete ESA medium with growth factors aSCF (avian stem cell factor), bFGF (basic fibroblast growth factor), IGF-1 (insulin-like growth factor-1) and LIF (leukemia inhibitory factor). The ARMA antibody is added in the proportion of 1 µg/ml final. The cells and colonies which are positive for alkaline phosphatase activity (AP+) are counted after 4 d of culture.

The results are depicted in FIG. 2.

In comparison with the various means described, such as the use of resin or of charcoal, and tested in an effort to control the level of retinoic acid in the medium, the addition of anti-retinoic acid antibody to the medium gives the best results as regards the quality and amount of the colonies present in the cultures.

Conclusion

The addition of anti-retinoic acid antibody to the culture medium significantly increases the presence and/or the maintenance of colonies having alkaline phosphatase activity.

III) Effect of Cytokines

We wanted to verify whether LIF or other cytokines of the same family could induce the proliferation of ES cells in birds.

Figure 3:
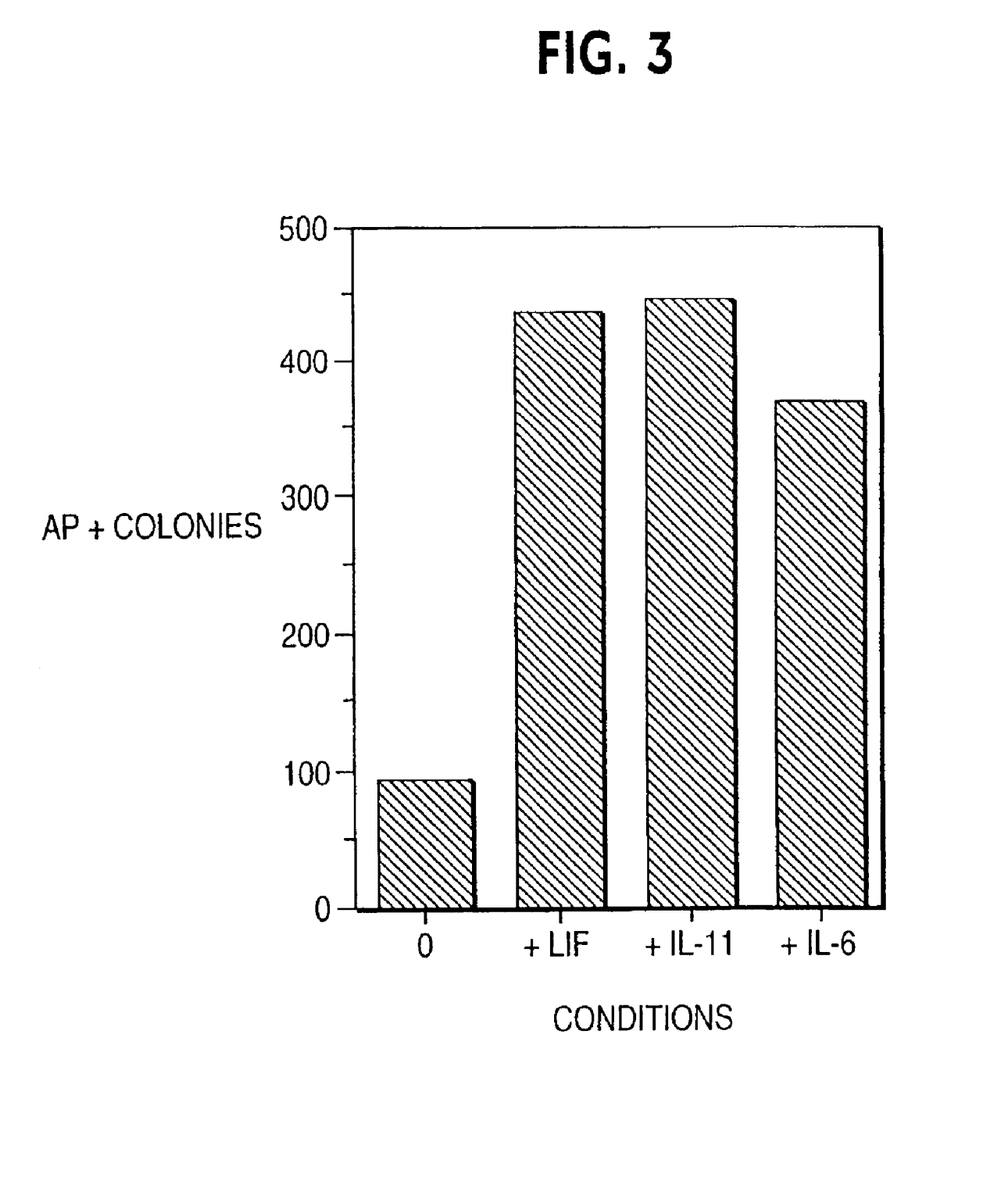
FIG. 3: Comparison of different cytokines quail blastoderms, 2 bl/ml base with gelatin 2- +3-d culture

The cells are inoculated in complete ESA medium with growth factors aSCF (avian stem cell factor), bFGF (basic fibroblast growth factor), IGF-1 (insulin-like growth factor1) in the presence of ARMA (1 µg/ml) and after the addition or otherwise of various cytokines of the same family, LIF (leukemia inhibitory factor), IL-11 (interleukin 11) and IL-6 (interleukin 6). In order to increase the adhesion and formation of alkaline phosphatase-positive colonies, as well as their size, a second inoculation takes place 2 days after the first one. The fixation, staining and reading of the colonies took place 3 days after the second inoculation.

The comparison of the effect of the various cytokines is depicted in FIG. 3 [sic.]

Conclusion

The role of the cytokines LIF, IL-11 and IL-6 seems especially marked and almost equivalent in the obtaining of colonies which are positive for alkaline phosphatase activity.

IV) Role of a Lawn of Feeder Cells

In mice, the growth of some ES cells requires the presence of a lawn of feeder cells. The effect of these cells on the bird embryo cells was tested.

Figure 4A:
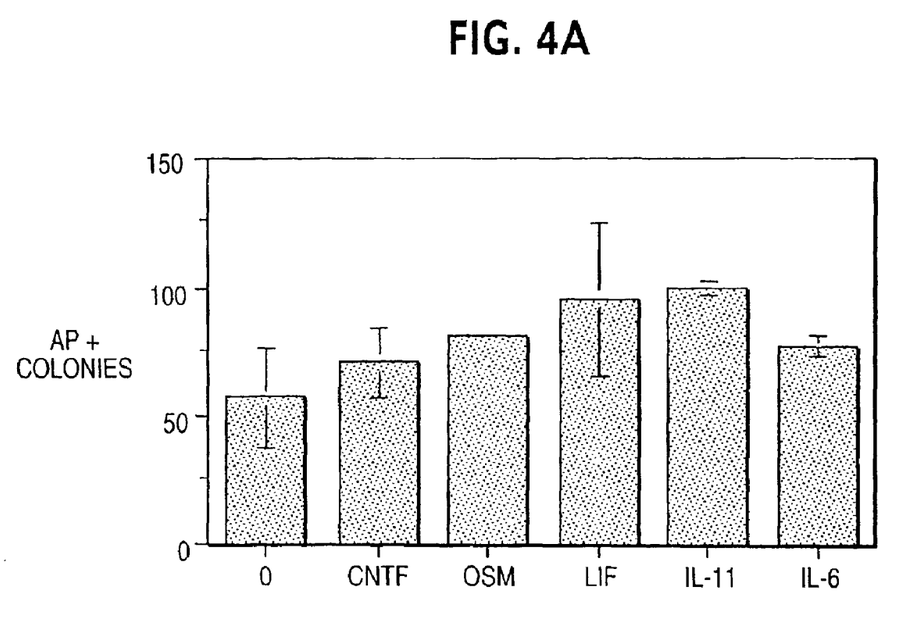
Figure 4B:
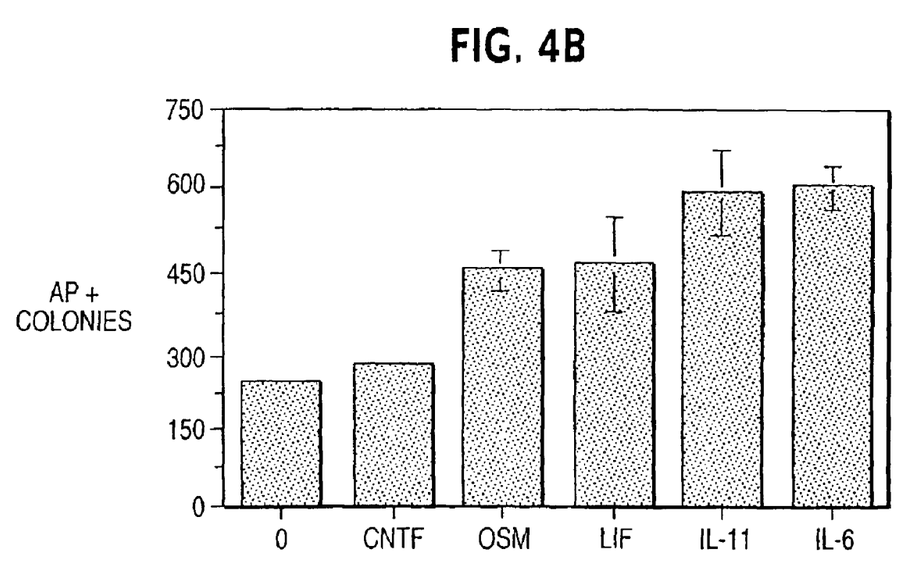

The cells are inoculated in complete ESA medium with growth factors aSCF (avian stem cell factor), bFGF (basic fibroblast growth factor), IGF-1 (insulin-like growth factor-1) and ARMA antibody (1 µg/ml), comparatively either onto a gelatin base or onto a lawn of mitomycin C-treated STO cells, as described in the Materials and Methods section. After three days of culture, a further inoculation is added to the culture. The cytokines CNTF (ciliary neurotrophic factor), OSM (oncostatin M), LIF (leukemia inhibitory factor), IL-11 (interleukin 11) and IL-6 (interleukin 6) are added to the medium at the concentrations stated above.

FIG. 4A depicts cell growth on gelatin in the presence of various cytokines. FIG. 4B depicts cell growth on a lawn of feeder cells in the presence of the same cytokines.

Conclusion

The number of colonies derived from the blastoderm cells and displaying alkaline phosphatase activity is very markedly increased in the presence of a lawn of feeder cells (approximately 4- to 5-fold), with a maintenance between the two systems of the same sensitivities with respect to the cytokines added to the medium. The cytokines LIF, IL-11 and Il-6 [sic] afford the best results for growth stimulation. In preliminary results, it is apparent, furthermore, that the combination of these 3 cytokines in complete ESA medium with factors produce [sic] very promising cumulative effects as regards the maintenance and proliferation of the colonies, with cells derived both from quail and chicken blastoderm disks.

V) Immunocytochemical Characteristics

Studies of reactivity with respect to various antibodies were carried out. The antibodies ECMA-7, SSEA-1 and SSEA-3, which are specific for a state of totipotency of murine ES cells, are capable of recognizing epitopes in the avian cell populations maintained in the cultures. To illustrate these recognitions by the antibodies, alkaline phosphatase activity and antibody double labelings demonstrate that all the cells or clumps of cells recognized by ECMA-7 display alkaline phosphatase activity. This property was observed with all the antibodies used, in varying degrees.

Approximately 20% of the colonies of alkaline phosphatase-positive cells are labeled with the antibody ECMA-7. This recognition suggests the presence in these clumps and under these culture conditions alone of cells having "ES" character. Nevertheless, a heterogeneity in the alkaline phosphatase-positive clumps implies variable degrees in the intensity of the "ES" character.

This distribution heterogeneity was observed on primary cultures. After subculturing, the proportion of positive cells, in particular for ECMA-7 but also for SSEA-1 and EMA-1, tends to increase very considerably to obtain very homogeneous cultures.

Figure 5A:
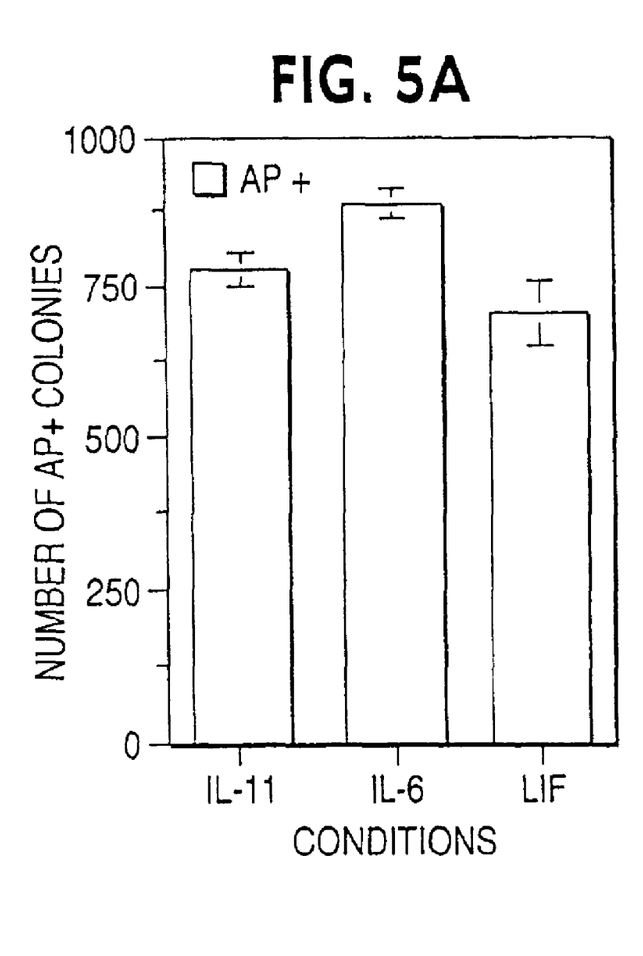
FIG. 5: Alkaline phosphatase activity and recognition by ECMA-7 quail blastoderms, 1.5 bl/ml base with STO cells
Figure 5B:
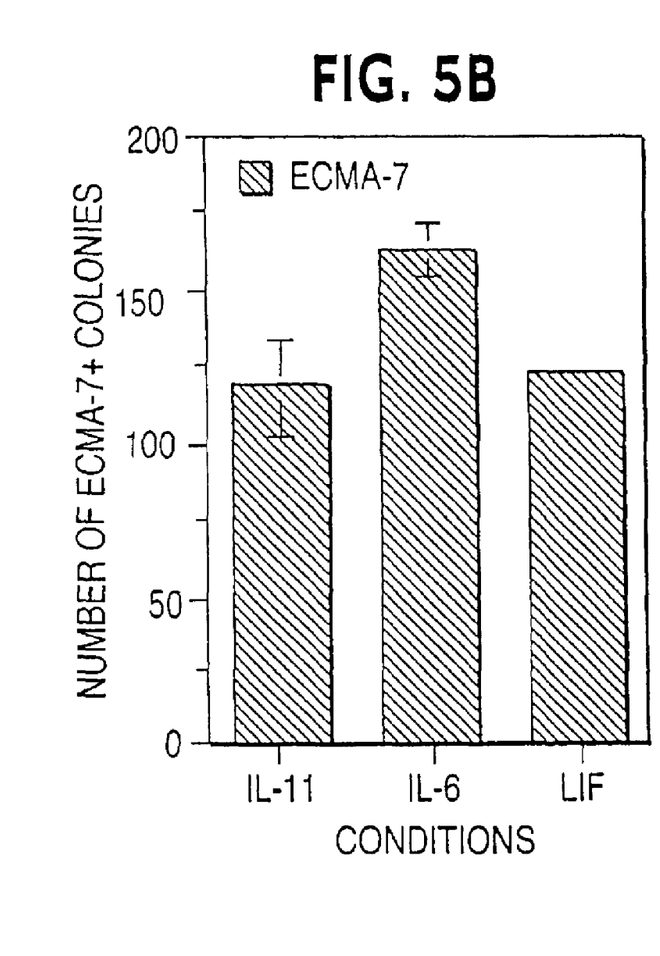

FIG. 5 shows, respectively, the alkaline phosphatase activity and the recognition by the antibody ECMA-7 of colonies of cells originating from the culture of quail blastoderms in the presence of various cytokines.

The antibodies SSEA-1 and SSEA-3, also used on murine ES cells, also recognize avian cells in the alkaline phosphatase-positive clumps.

The antibodies NC-1 and HNK-1, directed, respectively, from [sic] the epitopes of neural crest cells and of human natural killer cells, recognize, in fact, the same epitopes, and have been shown to recognize certain immature cells of the chicken blastoderm disk. In our system, these two antibodies recognize, here too, cells in clumps having alkaline phosphatase activity.

Figure 6:
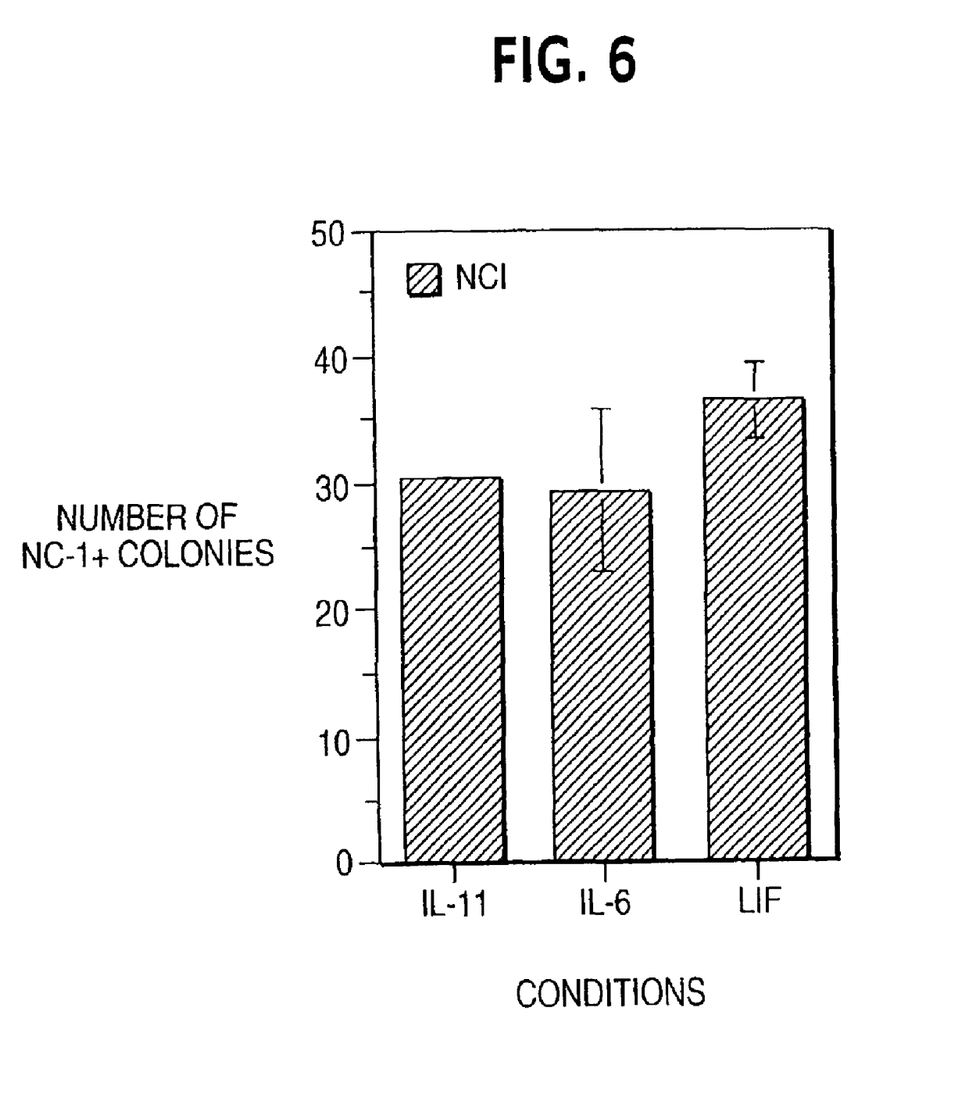
FIG. 6: Alkaline phosphatase activity and recognition by NC-1 quail blastoderms, 1.5 bl/ml base with STO cells

The results with NC-1 are depicted in FIG. 6.

The cells are inoculated in complete ESA medium with growth factors aSCF (avian stem cell factor), bFGF (basic fibroblast growth factor), IGF-1 (insulin-like growth factor-1) and ARMA antibody (1 µg/ml) on a lawn of mitomycin C-treated STO cells as described in the Materials and Methods section. After two days of culture, a further inoculation is added to the culture. The cytokines LIF (leukemia inhibitory factor), IL-11 (interleukin 11) and IL-6 (interleukin 6) are added to is the medium at the concentrations stated above. Double staining, alkaline phosphatase activity and detection of the epitopes by antibodies, is carried out according to the protocols presented above.

Moreover, the antibody EMA-1 (Hahnel and Eddy, 1986), initially directed against epitopes present on the primordial cells of the murine germ line, was used against these same cells in chickens. By testing this antibody in our culture system, we can demonstrate that EMA-1 recognizes cells and cell colonies all displaying alkaline phosphatase activity. It was, moreover, verified that this antibody EMA-1 recognizes murine ES cells only in their state of undifferentiated totipotency.

The antibodies were tested either on undifferentiated cultures obtained as described in Materials and Methods, or on cultures which were treated with an excess of retinoic acid added to the culture ($10^{-6}$ M) for at least 48 hours. The table below indicates the state of recognition by the various antibodies used.

| Monoclonal antibody | Undifferentiated | Differentiated |
| --- | --- | --- |
| ECHA-7 | + + + + + | – |
| SSEA-1 | + + + + + | – |
| SSEA-3 | + + + | – |
| TEC-01 | + + + + + | – |
| TEC-02 | + | + + + |
| TEC-03 | + + | + + |
| EMA-1 | + + + + | + |
| EMA-6 | + + + | + |
| TROMA-1 | – | + + + + |
| NC-1 | + + + + | + |
| HNK-1 | + + + + | + |

NC-1 and HNK-1 recognize the same epitopes
SSEA-1 and TEC 01 recognize the same epitopes It is apparent that the expression of ECMA-7 (Kemler et al. (1981)) is the largest, suggesting a genuine ES cell nature, and that TEC-01 (Draber et al. (1987)) and SSEA-1 (Solter and Knowles (1978)) recognize the same epitopes on undifferentiated cells exclusively. Conversely, the increase in expression of TEC-02 (Draber et al. (1987)) may, along such lines, indicate an induced or spontaneous state of differentiation. The completion of this loss of ES nature is characterized by the strong expression of TROMA-1 (Brulet et al. (1980)), present only on the differentiated cells. Hence this set of antibodies enables a picture to be built up regarding the state of differentiation of a culture. Antibodies such as TEC-03 (Draber et al. (1987)) are seen to be relatively indifferent to the marked state of differentiation.

It should, moreover, be stressed that, hitherto, neither ECMA-7 nor SSEA-1, SSEA-3, TEC-01, TEC-02, TEC-03 or TROMA-1 have been the subject of a publication demonstrating the reactivity on sections, cells or any material of avian origin.

Conclusion

Among the antibodies tested, some, such as ECMA-7 (Kemler et al. (1981)), SSEA-1 (Solter and Knowles (1978)), SSEA-3 (Shevinsky et al. (1982)), are characteristic of murine "ES" cells. These antibodies recognize cells which are hence potentially totipotent in avian cultures. The same observations having been obtained with either quail or hen cultures. [sic] Other antibodies, such as EMA-1 (Hahnel and Eddy (1986)), NC-1 and HNK-1 (Obo and Balch (1981)), are known to recognize avian epitopes (and murine in the case of EMA-1) of highly undifferentiated cells, and are hence also capable of recognizing a profile of avian stem cells.

VI) Subculturing of the Cells

Quail or chicken blastoderm disk cells are inoculated onto a lawn of STO feeder cells. After various days of culture, the cells are subcultured on a lawn of STO cells as described in Materials and Methods. The detection of cells and clumps which are positive both for alkaline phosphatase activity and for the colocalization of a labeling by ECMA-7 or NC-1 suggests that the culture conditions are defined for maintaining cells having totipotent character in the secondary and tertiary cultures. The process of subculturing brings about, moreover, once the first passage has been completed, a homogeneity in the whole of the culture, both morphologically and by the detection of the various epitopes. The clumps of cells become widely spread and homogeneous, a character enhanced by the large capacity of these cells to divide rapidly, in contrast to the differentiated cells present initially in the primary culture. To date, these identification and characterization criteria may be used and detected for at least 5 weeks after inoculation.

VII) Injection of the Cells into Recipient Embryos

The chicken blastoderm cells obtained in primary cultures or after successive subculturings may be injected into recipient embryos. In order to visualize rapidly a phenotypic contribution of the donor's cells in a recipient chick embryo, the cells maintained in culture originate from a pigmented strain and the recipient embryos from a nonpigmented strain. The cells maintained in cultures are dissociated and prepared as described in Materials and Methods, according to the same method as for a subculturing. The cell suspension is then prepared in the proportion of 1 to $3\times10^5$ cells per ml of ESA medium. The freshly laid, unincubated egg containing the recipient embryo is lightly irradiated with between 5 Gy and 7 Gy. A small window of a few $mm^2$ is made in the recipient's shell by grinding. The shell membrane is cut open with a scalpel and the cells are injected using a drawn-out capillary into the subgerminal cavity of the blastoderm disk in a volume of 1 to 5 $\mu l$, which corresponds to 100 to 1,500 cells at most. The average number of cells injected is 500 cells. The window is then covered with shell membranes and sealed. A piece of adhesive dressing is applied in order to complete the sealing and limit evaporation as far as possible. After 4 days of incubation under optimal conditions, the eggs are opened and the well-developed embryos are transferred to a larger shell and returned to incubation in order to finish their development in a satisfactory manner.

A number of animals were obtained in this way and show an apparent degree of chimerism, phenotypically detectable by the plumage marker used and characteristic of the strain of cells derived from the donor strain, varying from 5% to 90%. This chimerism can, until now, be obtained equally well with cells derived from primary, secondary or tertiary cultures. It should be noted that the percentages of chimeric animals and the degrees of chimerism of these animals do not vary substantially according to the time of culture of the injected cells. This further emphasizes the capacity of the medium and of the method described to maintain cells with a totipotent character.

EXAMPLE

Figure 7A:
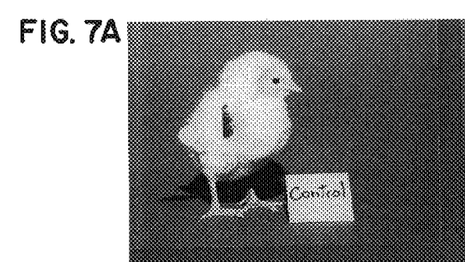
FIG. 7: Chimeric animals obtained by in ovo injection into embryos of cells maintained in culture. Cells injected after 8 or 10 days of culture.

Uninjected Control Animal (FIG. 7A)

Animal No. 1786–1787 showing a low degree of chimerism (5–10%)

Animal No. 1782–1783 showing a moderate degree of chimerism (50%)

Animal No. 1740–1741 showing a high degree of chimerism (90%)

Figure 7B:
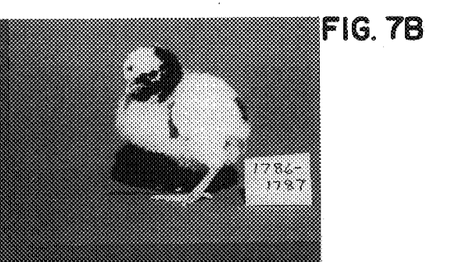
Figure 7C:
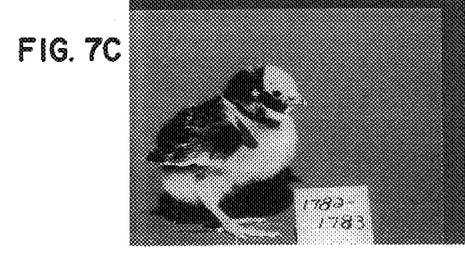
Figure 7D:
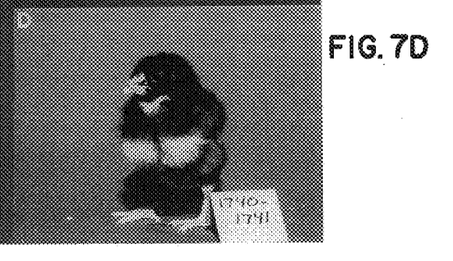

These animals are presented in FIGS. 7B to 7D.

References

Brulet et al. (1980). Proc. Natl. Acad. Sci. 77, 4113.
Draber et al. (1987). Cell Differentiation 21, 119.
Draber et al. (1987). Cell Differentiation 21, 227.
Hahnel and Eddy (1986). Gamete Research 15, 25.
Kemler et al. (1981). J. Embryo. Exp. Morph. 64, 45.
Obo and Balch (1981). J. Immunology 127, 1024.
Solter and Knowles (1978). Proc. Natl. Acad. Sci. 75, 5565.
Shevinsky et al. (1982). Cell 30, 697.
Tucker et al. (1984). Cell Differentiation 14, 223.
Urven et al. (1988). Development 103, 299.

What is claimed is:

1. A culture medium for avian embryonic stem cells, wherein said culture medium comprises:
   (a) basic fibroblast growth factor (bFGF);
   (b) IGF-1;
   (c) at least one cytokine selected from the group consisting of LIF, IL-11, IL-6, CNTF, and oncostatin M (OSM); and
   (d) stem cell factor (SCF),
   wherein said stem cell factor is either murine or avian stem cell factor (avian-SCF).

2. The culture medium of claim 1, further comprising feeder cells.

3. The culture medium of claim 1, further comprising at least one of the following compounds:
   (a) Fetal bovine serum;
   (b) Chicken serum;
   (c) Conalbumin;
   (d) Nonessential amino acids;
   (e) Sodium pyruvate;
   (b) Nucleoside stock;
   (g) Hepes;
   (h) β-Mercaptoethanol;
   (i) Penicillin;
   (j) Streptomycin; and
   (k) Gentamicin
   wherein the nucleoside stock comprises the mixture: adenosine, guanosine, cytidine, uridine, and thymidine in aqueous solution.

4. The culture medium of claim 1, further comprising an anti-retinoic acid antibody, wherein said anti-retinoic antibody neutralizes the differentiation activity of retinoic acid in said culture medium.

5. A method of culturing avian embryonic stem cells comprising:
   a) suspending said avian embryonic stem cells isolated from blastoderm disks of fertilized avian eggs in an avian culture medium comprising:
      (i) basic fibroblast growth factor (bFGF);
      (ii) IGF-1;
      (iii) at least one cytokine selected from the group consisting of LIF, IL-11, IL-6, CNTF, and oncostatin M (OSM); and
      (iv) stem cell factor (SCF);
   wherein said stem cell factor is either murine or avian stem cell factor (avian-SCF);
   b) inoculating a structural support with said avian embryonic stem cells suspended in step a), wherein said structural support is selected from the group consisting of feeder cells and gelatin; and
   c) culturing said avian embryonic stem cells.

6. The method of claim 5, wherein said avian embryonic stem cells obtained in step c) are alkaline phosphatase (AP) positive.

7. The method of claim 5, wherein an antibody selected from the group consisting of ECMA-7, SSEA-1, SSEA-3, TEC-01, EMA-1, and EMA-6 binds to said avian embryonic stem cells obtained in step c).

8. The method of claim 5, wherein said avian embryonic stem cells obtained in step c) do not bind TROMA-1.

9. A culture medium for avian embryonic stem cells, wherein said culture medium comprises bFGF, IGF-1, SCF, LIF, and IL-11.

10. The culture medium of claim 9, wherein said culture medium further comprises IL-6.

11. The culture medium of claim 10, wherein additional cytokines selected from the group consisting of CNTF and OSM, or anti-retinoic acid monoclonal antibody (ARMA), may be added to said culture medium.

* * * * *